[19] United States Patent
Davis et al.

[11] Patent Number: 4,908,144
[45] Date of Patent: Mar. 13, 1990

[54] DIMERCAPTOTHIADIAZOLE-DERIVED, ORGANIC ESTERS, AMIDES AND AMINE SALTS AS MULTIFUNCTIONAL ANTIOXIDANT/ANTIWEAR ADDITIVES

[75] Inventors: Robert H. Davis, Pitman; Liehpao O. Farng, Lawrenceville; Andrew G. Horodysky, Cherry Hill, all of N.J.

[73] Assignee: Mobil Oil Corporation, New York, N.Y.

[21] Appl. No.: 292,065

[22] Filed: Dec. 30, 1988

[51] Int. Cl.$^4$ ............................................. C01M 135/36
[52] U.S. Cl. ..................................... 252/47.5; 252/402; 548/127; 548/130; 548/142
[58] Field of Search ............... 252/47.5, 402; 548/142, 548/127, 130

[56] References Cited

U.S. PATENT DOCUMENTS

| | | | |
|---|---|---|---|
| 4,212,754 | 7/1980 | Chibnik | 252/49.7 |
| 4,568,472 | 2/1986 | Horodysky et al. | 252/49.6 |
| 4,584,114 | 4/1986 | Gemmill et al. | 252/47.5 |
| 4,661,273 | 4/1987 | Frangatos et al. | 252/47 |
| 4,678,592 | 7/1987 | Toukan | 252/25 |
| 4,761,482 | 8/1988 | Karol | 252/47.5 |
| 4,800,028 | 1/1989 | Loukan | 252/25 |

*Primary Examiner*—Jacqueline V. Howard
*Attorney, Agent, or Firm*—Alexander J. McKillop; Charles J. Speciale; Howard M. Flournoy

[57] ABSTRACT

Reaction products of Dimercaptothiadiazole-derived alcohols and alkenyl succinic anhydrides and their subsequent amine reaction products have been found to be effective antiwear/antioxidant multifunctional additives for lubricants.

36 Claims, No Drawings

DIMERCAPTOTHIADIAZOLE-DERIVED, ORGANIC ESTERS, AMIDES AND AMINE SALTS AS MULTIFUNCTIONAL ANTIOXIDANT/ANTIWEAR ADDITIVES

BACKGROUND OF THE INVENTION

This application is directed to dimercaptothiadiazole-derived reaction products which have multifunctional antioxidant/antiwear properties when incorporated into oleagenous compositions.

The use of dimercaptothiadiazole derivative, such as 2,5-dimercapto-1,3,4-thiadiazole, has been well known for their antioxidancy, anticorrosion, and metal passivation properties in a variety of lubricant applications, as disclosed in U.S. Pat. No. 4,661,273, U.S. Pat. No. 4,678,592 and U.S. Pat. No. 4,584,114.

The use of alkenyl succinic acid-esters has been reported as rust inhibitors and dispersants for many lubricating oils and greases.

The use of amine salts, such as amine phosphate salts, has found widespread commercial use for several decades as antiwear/EP additives.

Replacement of zinc phosphorodithioates by zinc/-phosphorus-free antiwear additives in engine oils, circulating oils, gear oils and various other lubricating systems is currently considered desirable. The products of the present invention provide outstanding FZG gear performance, low four-ball wear and good antioxidant activity, and most important, are zinc/phosphorus free. Therefore, these products are good canditates for the replacement of zinc phosphorodithioates in many lubricant formulations.

SUMMARY OF THE INVENTION

It has now been found that lubricant compositions containing small additive concentrations of dimercaptothiadiazole-derived esters, amides and amine salts or mixtures thereof possess excellent antiwear and extreme pressure properties coupled with good antioxidant activity. Both the dimercaptothiadiazole moiety and the amine/amide/ester moieties are believed to provide the basis for the synergistic antiwear activity. The dimercaptothiadiazole group is believed to contribute additional metal passivation and antioxidation properties to these novel additives. The succinic anhydride derived acid-ester moieties may additionally contribute significant antirust properties to this new class of additives.

All of these beneficial properties are believed to be enhanced by this novel internal synergism. This unique internal synergism concept is believed to be applicable to similar structures containing (a) dimercaptothiadiazole-derived alcohol groups, (b) alkenyl succinic groups, and (c) amine/amide/ester/acid linkages within the same molecule. The products of this patent application show good stability and compatibility when used in the presence of other commonly used additives in lubricant compositions.

Accordingly, the present invention is particularly directed to dimercaptothiadiazole-derived alcohol/succinic anhydride reaction products, their subsequent amine reaction derivatives and their use as antiwear and antioxidant additives having rust inhibiting properties when incorporated into various oleageneous media such as oils of lubricating viscosity and greases made therefrom.

DESCRIPTION OF PREFERRED EMBODIMENT

The use of additive concentrations of the hereindescribed dimercaptothiadiazole-derived esters, amides and amine salts in premium quality automotive and industrial lubricants significantly enhances the stability, improves load-carrying, reduces the wear, and extends service life. These novel compositions are useful at low concentrations and do not contain any potentially undesirable metals or phosphorus. These multifunctional antioxidants can be commercially made using an economically favorable process.

The products of reactions described in the present patent application may be advantageously made as set forth herein below.

2,5-Dimercapto-1,3,4-thiadiazole (made by the reaction of hydrazine with carbon disulfide) was reacted with hydrocarbylene oxides optionally containing additional oxygen, sulfur-nitrogen dimercaptothiadiazole-derived alcohols. These alcohols were then reacted with hydrocarbylene succinic anhydrides to form succinic acid/esters. Thereafter, these acid/esters were subsequently reacted with various amines converting them to ammonium salt/amide/ester/acid derivatives, as generally described below:

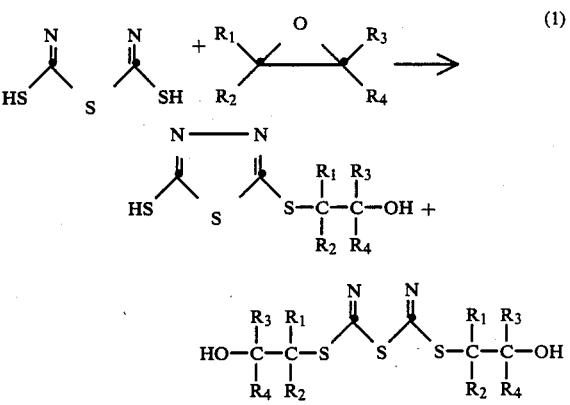

or more generally displayed as:

where $R_1$, $R_2$, $R_3$ and $R_4$ are independently hydrogen, or $C_1$ to about $C_{30}$ hydrocarbyl and optionally contain additional sulfur, oxygen or nitrogen. R' represents the dimercaptothiadiazole-derived moiety.

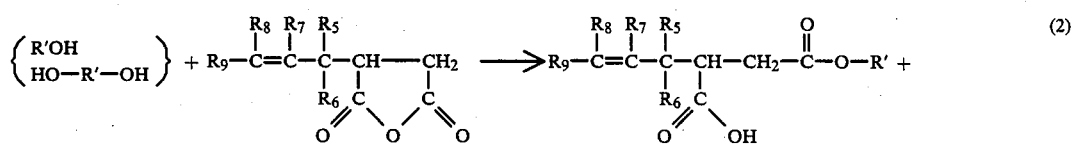

-continued

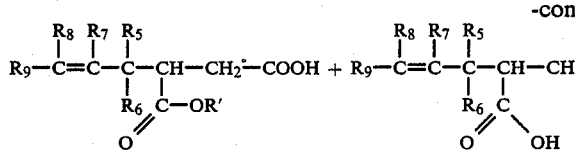

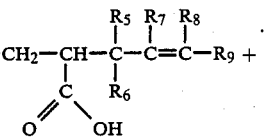

where $R_5$ to $R_8$ are independently hydrogen or hydrocarbyl, aralkyl, or cycloakyl groups of $C_1$ to about $C_{10}$ and $R_9$ is a hydrocarbon based group of $C_1$ to about $C_{60}$.

R' as noted hereinabove represents the dimercaptothiadiazolederived moiety.

The epoxidation of the dimercaptothiadiazole may use up to two molar quantities of hydrocarbylene oxide, and similarly, the reaction with alkenyl-succinic anhyride may also use up to two molar quantities of anhydride.

These substituted succinic acid-ester derivatives were subsequently converted to their amine salts/amide-ester/amide-acid derivatives by reaction with almost molar quantities, or less than molar quantities, or more than molar quantities of amines (Equation 3).

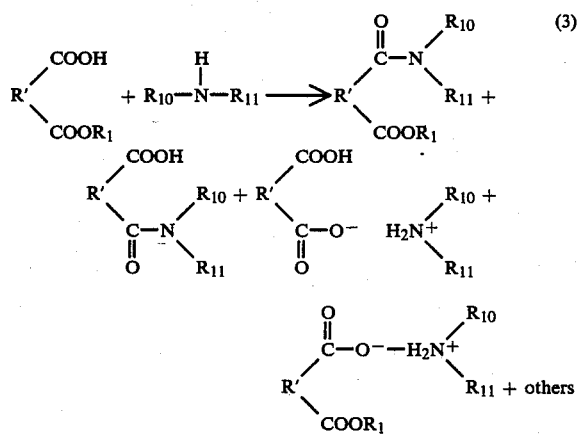

where $R_{10}$, $R_{11}$ are independently hydrogen or hydrocarbyl, aralkyl, aryl, or cycloalkyl groups of $C_1$ to about $C_{60}$, or hydrocarboxy hydrocarbylene groups and R' represents the DMTD derived moiety.

Any appropriate mercapto-thiadiazole may be used herein. However, preferred is 2,5-dimercapto-1,3,4-thiadiazole. Some suitable examples include but are not limited to 3,4-dimercapto-1,2,5-thiadiazole, 3,5-dimercapto-1,2,4-thiadiazole, 4,5-dimercapto-1,2,5-thiadiazole, 4,5-dimercaptobenzo 1,2,3-thiadiazole, 4,7-dimercaptobenzo 1,2,3-thiadiazole, 4,6-dimercaptobenzo 1,2,3-thiadiazole, 5,6-dimercaptobenzo 1,2,3-thiadiazole, 5,7-dimercaptobenzo 1,2,3-thiadiazole, 6,7-dimercaptobenzo 1,2,3-thiadiazole, 4,5-dimercaptobenzo 2,1,3-thiadiazole, 4,6-dimercaptobenzo 2,1,3-thiadiazole, 5,6-dimercaptobenzo 2,1,3-thiadiazole, 5,7-dimercaptobenzo 2,1,3-thiadiazole, 6,7-dimercaptobenzo 2,1,3-thiadiazole.

Suitable epoxides are disclosed by the formula described in Equation 1 above. Preferred is 1,2-epoxybutane. However, included within the scope of these epoxides are 1,2-epoxydecane, 1,2-epoxydodecane, 1,2-epoxytetradecane, 1,2-epoxypentadecane, 1,2-epoxyhexadecane, 1,2-epoxyheptadecane, 1,2-epoxyoctadecane, 1,2-epoxyeicosane, 1,2-epoxybutane, 1,2-epoxypropane, 1,2-epoxyethane, and mixtures of such epoxides or epoxidized oils including epoxidized soybean oil and epoxidized linseed oil.

Hydrocarbyl as used herein includes but is not limited to alkyl, aryl, alkaryl, aralkyl, alkenyl, cycloalkyl or cycloalkenyl groups containing from 8 to about 30 carbon atoms, preferred are 10 to 22 carbon atoms. Preferably, hydrocarbyl is an alkyl or aryl, or aralkyl group. Suitable amines include any such hydrocarbyl amine, e.g., polyethylene amines, polypropylene amines, primary or secondary, straight and branched chain amines and alkenyl succinimides.

$C_1$ to about $C_{200}$ alkenyl succinic anhydrides having a molecular weight of from about 400 to about 5,000 are suitable for use herein as well as their corresponding acids. Preferred is dodecenyl succinic anhydride.

The molar ratio of the varius reactants may vary from 10:10:1:1 to 1:100:100:100 and preferably 2:2:1:1 to 1:2:2:2 of thiadiazoles:oxides:succinic acid-esters:amines. The reaction sequence has been generally disclosed to be (1) the reaction of DMTD with an alkylene oxide to form DMTD-derived alcohols which are (2) then reacted with alkenyl succinic anhydrides to form succinic acid/esters which are thereafter (3) reacted with various amines to obtain ammonium salt-/amide/ester/acid derivatives. It is understood, however, that the invention is not limited to this sequence. Any convenient sequence may be used or the reactants may be mixed in a single step. Usually the reaction temperature (Equation 1–3) may vary from about 50° C. to about 300° C. and the time from about 0.5 to about 10 hours or more; the pressure is preferably ambient, although higher pressures may be used if thought desirous. The reaction conditions are dependent upon the specific reactants used.

When a solvent is thought desirable, a suitable hydrocarbon solvent such as toluene may be used.

The following examples are meant to illustrate the invention and in no way to limit it.

EXAMPLE 1

DMTD-Butylene Oxide-DDSA-Aniline Adduct 60.0 grams (0.4 mole) of 2,5-dimercapto 1,3,4-thiadiazole (commercially obtained) was charged in to a one liter reactor equipped with dropping funnel, reflux condensor, thermometer, and mechanical stirrer. Approximately 200 milliliters toluene was added into the reactor to make a suspension.

Approximately 60.6 grams (0.84 mole) of 1,2-epoxybutane was cautiously added dropwise to the suspension at 50°–60° C. over a course of one hour. The reaction exotherm was controlled by using ice-water bath for cooling. Approximately 55° C. initial temperature is required to activate the reaction.

At the end of the addition, 218.0 grams (0.82 mole) of dodecenyl succinic anhydride was added to the butoxylated DMTD product. A nitrogen sparger inlet was used to replace the dropping funnel in the four-neck reactor. This mixture was heated at 118°±2° C. for two hours and at the end of the reaction, it was cooled down to ambient temperature as a yellow, viscous liquid. The excess unreacted butylene oxide was collected in the Dean Stark trap equipped with a condenser.

Approximately 74.4 grams (0.8 mole) of aniline was added to the above liquid. This reaction mixture was heated up to 118°±2° C. for seven hours. Approximately 8 milliliters of water was collected in the Dean Stark trap. It was further refluxed for three more hours and then the volatiles were stripped under house vacuum (250 to 300 mm/HG) leaving a very viscous material as the desired product. It was further purified by hot filtration through super-cel.

| Nitrogen analysis | 5.41% (theory 5.7%) |
| Sulfur analysis | 7.54% (theory 9.84%) |

EXAMPLE 2

DMTD-Butylene Oxide-DDSA-Primene 81R

This reaction follows a similar fashion as Example 1 but with use of an alternate amine.

60.0 Grams (0.4 mole) of DMTD was reacted with 60.6 grams (0.84 mole) of 1,2-epoxybutane at 50°–60° C. for one hour.

At the end of the addition of butylene oxide, 213.0 grams (0.80 mole) of dodecenyl succinic anhydride (DDSA) was added and this mixture was heated up to 100° C. and maintained at that temperature for three hours.

After cooling down to ambient temperature, a one-half portion of the intermediate adduct (0.2 mole) and 76.4 grams of Primene 81R (0.4 mole) were mixed together in a one liter flask. This mixture was refluxed at 115°±30° C. for four hours. Then the volatiles were stripped under house vacuum leaving a viscous, yellow liquid as the final adduct (236.4 grams).

* Primene 81R amine is a proprietary amine commercially obtained from Rohm & Haas Chemical Company. It is believed to be a mixture of primary aliphatic amines of predominantly $C_{12}$ to $C_{14}$ tertiary-alkyl groups. It is more fully described in U.S. Pat. No. 3,224,957.

EVALUATION OF THE PRODUCTS

Each of the dimercaptothiadiazole-derived products were blended into fully formulated oils and evaluated for both antioxidant performance and antiwear activity as shown below.

The products of examples were blended into fully formulated heavy lubricating oils and evaluated for their load-carrying capability by FZG Gear tester, and antioxidant activity by Catalytic Oxidation Test at 325° F. for 40 hours.

The formulation was tested for gear wear protection according to the FZG Gear Test (DIN-51.354). In this test, dip-lubricated gears are weighed and operated at a fixed speed and fixed initial oil temperature (90° C.) in the gear oil under test. The load on the teeth is increased in increments. After each load stage, the weight changes are determined and recorded. The results are reported in Table 1. The higher the Fail Stage value the better the material. The lower the wear value the better the product.

TABLE 1

| Example No. | Additive Conc. (wt. %) | FZG Fail Stage | Oxidation Test Change in Acid Number | Percent Change in Viscosity |
|---|---|---|---|---|
| Base Oil (fully formulated, solvent refined heavy bright oil) | — | 9 | 6 | 45 |
| Example 1 in above Base Oil | 1.0 | 13 | 3.1 | 45 |
| Example 2 in above Base Oil | 1.0 | 13 | 7.1 | 41 |

As shown above, the products of this invention show very good antiwear, extreme pressure activities as evidenced by improving wear characteristics and scoring-load capacity from state 9 to stage 13 in FZG tester. Also, the antioxidant activity is indicated by control of increase in acidity and viscosity.

The product of Example 2 was also evaluated for antiwear performance in industrial oils using the Four-Ball Test (Table 2).

Four-Ball Wear Test using a 60 kg load at 1,000 rpm and 200° F., 2,000 rpm and 200° F.; and at 1,000 rpm and 300° F., for 30 minutes as shown in Table 2.

In the Shell Four-Ball Wear Test, three stationary balls are placed in the lubricant cup and the lubricant containing the compound to be tested is added thereto, and a fourth ball is placed in a chuck mounted on a device wich can be used to spin the ball at known speeds and loads. The samples were tested using ½ inch stainless steel balls of 52100 steel for 30 minutes.

TABLE 2

| | Four-Ball Test Wear Scar Diameter in mm, 30 Minute Test 60 kg Load | | |
|---|---|---|---|
| Example No. | 1000 rpm 200° F. | 2000 rpm 200° F. | 1000 rpm 300° F. |
| Base Oil (80% solvent paraffinic bright, 20% solvent paraffinic neutral mineral oils) | 1.91 | 2.63 | 1.95 |
| 1% Example 2 in above Base Oil | 0.59 | 0.88 | 0.75 |

As can be seen from the above wear test results, the product exhibits considerable antiwear activity.

The products of the examples were also evaluated by the Catalytic Oxidation Test at 375° F. for 24 hours in different industrial oil formulations (Table 3). Basically, in the catalytic oxidation test, the lubricant is subjected to a stream of air which is bubbled through at the rate of five liters per hour at elevated temperatures for a specified time (Table 3, 375° F. for 24 hours). Present in the composition are samples of metals commonly used in engine construction, namely, iron, copper, aluminum, and lead. See U.S. Pat. No. 3,682,980, incorporated herein by reference.

TABLE 3

| Example No. | Catalytic Oxidation Test | | | |
| --- | --- | --- | --- | --- |
| | Additive Conc. (wt %) | Change in Acid Number ΔTAN | % Change in Viscosity ΔKV | Sludge |
| Base Oil (150 second, fully formulated, solvent refined paraffinic bright oil containing defoamant/demulsifier/antiwear/anticorrosion/EP/antitrust performance package. | — | 6.53 | 177.9 | medium |
| Example 1 in above Base Oil | 1.0 | 4.89 | 157.8 | light |
| Example 2 in above Base Oil | 1.0 | 3.02 | 117.2 | light |

Clearly the use of these dimercaptothiadiazole derived alcohol/succinic anhydride reaction products and their subsequent amine reaction derivatives provides exceptional antiwear and antioxidant activity with potential rust inhibiting property.

The additives embodied herein are utilized in lubricating oil or grease compositions in an amount which imparts significant antiwear characteristics to the oil or grease as well as reducing the friction of engines operating with the oil in its crankcase. Concentrations of about 0.0001 to about 10 wt. % based on the total weight of the composition can be used. Preferably, the concentration is from about 0.1 to about 3 wt. %. It is expected that these materials would also be suitable for use in liquid hydrocarbyl or alcoholic or mixed hydrocarbyl/alcoholic fuel compositions.

The additives have the ability to improve the antiwear characteristics and friction reducing characteristics of various oleogenous materials such as hydrocarbyl lubricating media which may comprise liquid oils in the form of either a mineral oil or a synthetic oil, or in the form of a grease in which the aforementioned oils are employed as a vehicle.

In general, mineral oils, both paraffinic, naphthenic and mixtures thereof, employed as the lubricant, or grease vehicle, may be of any suitable lubricating viscosity range, as for example, from about 45 SSU at 100° F. to aobut 6000 SSU at 100° F. to about 6000 SSU at 100° F. and preferably, from about 50 to about 250 SSU at 210° F. These oils may have viscosity indexes ranging to about 95 are preferred. The average molecular weights of these oils may range from about 250 to about 800. Where the lubricant is to be employed in the form of a grease, the lubricating oil is generally employed in an amount sufficient to balance the total grease composition, after accounting for the desired quantity of the thickening agent, and other additive components to be included in the grease formulation.

A wide variety of materials may be employed as thickening or gelling agents. These may include any of the conventional metal salts or soaps, which are dispersed in the lubricating vehicle in grease-forming quantities in an amount to impart to the resulting grease composition the desired consistency. Other thickening agents that may be employed in the grease formulation may comprise the non-soap thickeners, such as surface-modified clays and silicas, aryl ureas, calcium complexes and similar materials. in general, grease thickeners may be employed which do not melt and dissolve when used at the required temperature within a particular environment; however, in all other respects, any materials which is normally employed for thickening or gelling hydrocarbon fluids for foaming grease can be used in preparing grease in accordance with the present invention.

In instances where synthetic oils, or synthetic oils employed as the vehicle for the grease, are desired in preference to mineral oils, or in combination therewith, various compounds of this type may be successfully utilized. Typical synthetic vehicles include, but are not limited to, polyisobutylene, polybutenes, hydrogenated polydecenes, polypropylene glycol, polyethylene glycol, trimethylolpropane esters, neopentyl and pentaerythritol esters, di(2-ethylhexyl) sebacate, di(2-ethylhexyl) adipate, dibutyl phthalate, fluorocarbons, silicate esters, silanes, esters of phosphorus-containing acids, liquid ureas, ferrocene derivatives, hydrogenated synthetic oils, chain-type polyphenyls, siloxanes and silicones (polysiloxanes), alkyl-substituted diphenyl esters typified by a butyl-substituted bis(p-phenoxy phenyl) ether, phenoxy phenylethers.

It is to be understood, however, that the compositions contemplated herein can also contain other materials. For example, corrosion inhibitors, extreme pressure agents and the like can be used as exemplified respectively by metallic phenates of sulfonates, polymeric succinimides, metallic phenates of sulfonates, polymeric succinimides, non-metallic or metallic phosphorodithioates and the like. These materials do not detract from the value of the compositions of this invention, rather the materials serve to impart their customary properties to the particular compositions in which they are incorporated.

Although the present invention has been described with preferred embodiments, it is to be understood that modifications and variations may be resorted to, without departing from the spirit and scope of this invention, as those skilled in the art will readily understand. Such modifications and variations are considered to be within the purview and scope of the appended claims.

We claim:

1. A product of reaction having multifunctional antiwear/antioxidant characteristics when admixed with various lubricating media prepared by reacting (1) a dimercaptothiadiazole with an epoxide to form dimercaptothiadiazole-derived alcohols which are thereafter (2) reacted with hydrocarbyl succinic anhydrides to form succinic acid esters which are thereafter (3) reacted with hydrocarbyl amines to produce the desired ammonium salt/amine/ester/acid derivative and wherein the reaction temperatures vary from about 50 to about 300° C., the pressure varies from ambient to slightly higher and the reaction time varies from about 0.5 to about 10 hours or more.

2. The product of claim 1 wherein the amount of dimercaptothiadiazole to epoxide to alkenyl succinic anhydride acid/esters to amine varies from about 10:10:1:1 to about 1:100:100:100 moles.

3. The product of claim 2 wherein said molar ratio varies from about 2:1:1:1 to about 1:2:2:2.

4. The product of claim 1 wherein the dimercaptothiadiazole is selected from the group consisting of 3,4-dimercapto-1,2,5-thiadiazole, 3,5-dimercapto-1,2,4-thiadiazole, 4,5-dimercapto-1,2,5-thiadiazole, 4,5-dimercaptobenzo 1,2,3-thiadiazole, 4,7-dimercaptobenzo 1,2,3-thiadiazole, 4,6-dimercaptobenzo 1,2,3-thiadiazole, 5,6-dimercaptobenzo 1,2,3-thiadiazole, 5,7-dimercaptobenzo 1,2,3-thiadiazole, 6,7-dimercaptobenzo 1,2,3-thiadiazole, 4,5-dimercaptobenzo 2,1,3-thiadiazole, 4,6-dimercaptobenzo 2,1,3-thiadiazole, 5,6-dimercaptobenzo 2,1,3-thiadiazole, 5,7-dimercaptobenzo 2,1,3-thiadiazole, 6,7-dimercaptobenzo 2,1,3-thiadiazole, and 2,5-dimercapto-1,3,4-thiadiazole.

5. The product of claim 4 wherein the dimercaptothiadiazole is 2,5-dimercapto 1,3,4-thiadiazole.

6. The product of claim 1 wherein the alkenyl oxide is selected from the group consisting of 1,2-epoxydodecane, 1,2-epoxytetradecane, 1,2-epoxypentadecane, 1,2-epoxyhexadecane, 1,2-epoxypropane, 1,2-epoxyethane, 1,2-epoxyheptadecane, 1,2-epoxyoctadecane, 1,2,epoxyeicosane and 1,2-epoxybutane and mixtures of such, or epoxidized soybean or epoxidized linseed oil.

7. The product of reaction of claim 6 wherein the alkenyl oxide is 1,2-epoxybutane.

8. The product of reaction of claim 1 wherein the hydrocarbyl succnic anhydride is selected from $C_6$ to about $C_{18}$ alkenyl succinic anhydrides.

9. The product of reaction of claim 8 wherein the succinic anhydride is dodecenyl succinic anhydride.

10. The product of reaction of claim 1 wherein the amine is selected from the group consisting of hydrocarbyl amines wherein hydrocarbyl includes alkyl, alkenyl, aryl, aralkyl, alkaryl, cycloakyl, including primary and secondary amines straight and branched chained amines and mixtures thereof.

11. The product of reaction of claim 10 wherein the amine is aniline.

12. The product of reaction of claim 10 wherein the amine is a mixture of primary aliphatic amines.

13. A lubricant composition comprising a major amount of and oil of lubricating viscosity or grease prepared therefrom and a minor amount of a product of reaction by reacting (1) a dimercaptothiadiazole with an epoxide to form dimercaptothiadiazole-derived alcohols which are then (2) reacted with hydrocarbyl succinic anhydrides to form succinic acid esters which are thereafter (3) reacted with suitable amines to produce the desired ammonium salt/amine/ester/acid derivatives.

14. The lubricant composition of claim 13 wherein the dimercaptothiadiazole is selected form the group consisting of 3,4-dimercapto-1,2,5-thiadiazole, 3,5-dimercapto- 1,2,4-thiadiazole, 4,5-dimercapto-1,2,5-thiadiazole, 4,5-dimercaptobenzo 1,2,3-thiadiazole, 4,7-dimercaptobenzo 1,2,3-thiadiazole, 4,6-dimercaptobenzo 1,2,3-thiadiazole, 5,6-dimercaptobenzo 1,2,3-thiadiazole, 5,7-dimercaptobenzo 1,2,3-thiadiazole, 6,7-dimercaptobenzo 1,2,3-thiadiazole, 4,5-dimercaptobenzo 2,1,3-thiadiazole, 4,6-dimercaptobenzo 2,1,3-thiadiazole, 5,6-dimercaptobenzo 2,1,3-thiadiazole, 5,7-dimercaptobenzo 2,1,3-thiadiazole, 6,7-dimercaptobenzo 2,1,3-thiadiazole and 2,5-dimercapto- 1,3,4-thiadiazole.

15. The lubricant composition of claim 14 wherein the dimercaptothiadiazole is 2,5-dimercapto 1,3,4-thiadiazole.

16. The lubricant composition of claim 13 wherein the alkylene oxide is selected from the group consisting of 1,2-epoxydodecane, 1,2-epoxytetradecane, 1,2-epoxypentadecane, 1,2-epoxyhexadecane, 1,2-epoxypropane, 1,2-epoxyethane, 1,2-eopoxyheptadecane, 1,2-epoxyoctodecane, 1,2,epoxyeicosane and 1,2-epoxybutane and mixtures of suchor epoxidized soybean or epoxidized linseed oil.

17. The lubricant composition of claim 13 wherein the alkenyl oxide is 1,2-epoxybutane.

18. The lubricant composition of claim 13 wherein the alkenyl succinic anhydride is selected from $C_6$ to about $C_{18}$ alkenyl succinic anhydrides.

19. The lubricant composition of claim 18 wherein the succinic anhydride is dodecenyl succinic anhydride.

20. The lubricant composition of claim 13 wherein the amine is selected from the group consisting of hydrocarbyl amines wherein hydrocarbyl includes alkyl, alkenyl, aryl, aralkyl, alkaryl, cycloakyl, including primary and secondary amines straight and branched chained amines and mixtures thereof.

21. The lubricant composition of claim 20 wherein the amine is aniline.

22. The lubricant composition of claim 20 wherein the amine is a mixture of primary aliphatic amines.

23. The lubricant composition of claim 14 wherein said major amount is an oil of lubricating viscosity selected from the group consisting of (1) mineral oils, (2) synthetic oils and (3) mixtures of mineral and synthetic oils or a grease prepared from any one of (1), (2) or (3).

24. The lubricant composition of claim 23 wherein said oil is a mineral oil.

25. The lubricant composition of claim 23 wherein said oil is a synthetic oil.

26. The lubricant composition of claim 24 wherein said oil is a mixutre of mineral and synthetic oils.

27. The lubricant composition of claim 13 wherein said oil is a grease.

28. The lubricant composition of claim 13 containing from about 0.01 to about 10 wt % of said product.

29. A product of reaction prepared by reacting (1) a dimercaptothiadiazole with an alkylene oxide to form dimercaptothiadiazole-derived alcohols which are thereafter (2) reacted with alkenyl succinic anhydrides to form succinic acid esters which are thereafter (3) reacted with suitable amines to produce the desired ammonium salt/amine/ester/acid derivative as generally described below:

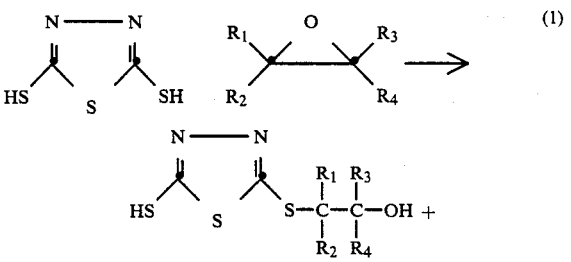

-continued

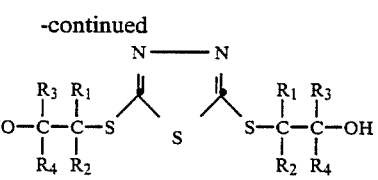

or:

R'OH and HO—R'—OH

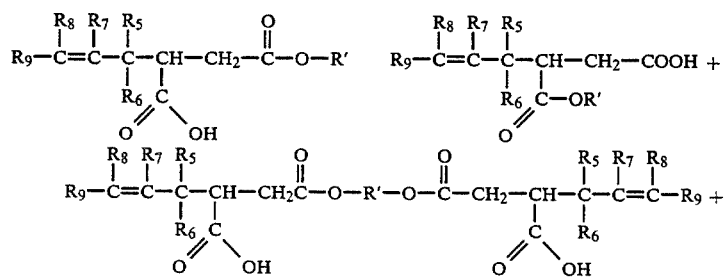

other structures ≡ $\begin{array}{c} \diagup COOH \\ R' \\ \diagdown COOR_1 \end{array}$ (3)

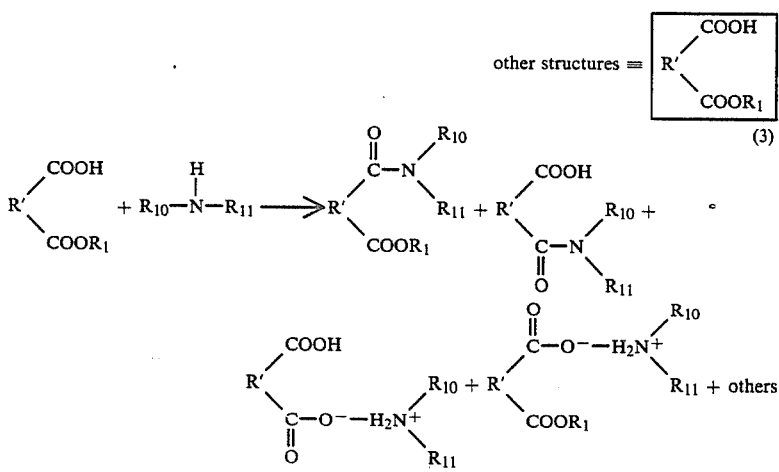

where $R_1$, $R_2$, $R_3$ and $R_4$ are independently hydrogen, or $C_1$ to about $C_{30}$ hydrocarbyl and optionally contain additional sulfur, oxygen or nitrogen, and where R' represents the dimercaptothiadiazole-derived moiety, where $R_5$ to $R_8$ are independently hydrogen or hydrocarbyl, aralkyl, or cycloakyl groups of $C_1$ to about $C_{10}$ and $R_9$ is a hydrocarbon based group of $C_1$ to about $C_{60}$ and where $R_{10}$, $R_{11}$ are independently hydrogen or hydrocarbyl, aralkyl, aryl, or cycloalkyl groups of $C_1$ to about $C_{60}$, or hydrocarboxy hydrocarbylene groups.

30. The product of reaction of claim 29 wherein the alkylene oxide is 1,2-epoxybutane.

31. The product of reaction of claim 29 wherein the alkenyl succinic anhydride is selected from $C_6$ to about $C_{18}$ alkenyl succinic anhydrides.

32. The product of reaction of claim 31 wherein the succinic anhydride is dodecenyl succinic anhydride.

33. The product of reaction of claim 29 wherein the amine is aniline.

34. The product of reaction of claim 29 wherein the amine is Primene 81R.

35. A zinc/phosphorus-free lubricating oil comprising a major amount of an oil of lubricating viscosity and a minor amount of a product as described in claim 1.

36. A zinc/phosphorus-free lubricating oil comprising a major amount of an oil of lubricating viscosity and a minor amount of a product of reaction as described in claim 29.

* * * * *